(12) United States Patent
De Jonge et al.

(10) Patent No.: US 7,325,443 B2
(45) Date of Patent: Feb. 5, 2008

(54) SAMPLING DEVICE AND METHOD FOR MEASURING FLUID FLOW AND SOLUTE MASS TRANSPORT

(75) Inventors: Hubert De Jonge, Viborg (DK); Gadi Rothenberg, Amsterdam (NL)

(73) Assignee: Aahus Universitet, Arhus (DK)

( * ) Notice: Subject to any disclaimer, the term of this patent is extended or adjusted under 35 U.S.C. 154(b) by 248 days.

(21) Appl. No.: 10/514,314

(22) PCT Filed: May 15, 2003

(86) PCT No.: PCT/IB03/01874

§ 371 (c)(1),
(2), (4) Date: Jun. 22, 2005

(87) PCT Pub. No.: WO03/098167

PCT Pub. Date: Nov. 27, 2003

(65) Prior Publication Data

US 2005/0235757 A1    Oct. 27, 2005

(30) Foreign Application Priority Data

May 15, 2002 (SE) .................................. 0201485

(51) Int. Cl.
*G01F 1/704* (2006.01)
*G01V 9/02* (2006.01)
*G01P 13/00* (2006.01)

(52) U.S. Cl. ................. 73/61.72; 73/64.56; 73/861.07; 73/863.23

(58) Field of Classification Search ............... 73/61.71, 73/61.72, 61.73, 64.56, 861.07, 863.23, 863.41, 73/863.51, 863.52, 864, 864.71
See application file for complete search history.

(56) References Cited

U.S. PATENT DOCUMENTS 5,355,736 A    10/1994    Skogley ................... 73/863.21
6,401,547 B1 *    6/2002    Hatfield et al. .......... 73/861.04

FOREIGN PATENT DOCUMENTS

| DE | 201 16 283 | 2/2002 |
|---|---|---|
| WO | 97/46853 | 12/1997 |
| WO | 01/33173 | 5/2001 |

* cited by examiner

*Primary Examiner*—Daniel S. Larkin
(74) *Attorney, Agent, or Firm*—Young & Thompson

(57) ABSTRACT

A device and a method for measuring fluid flow and solute mass transport in flow systems includes a casing (1) having inlet (3) and outlet (9) openings and a fluid passageway therebetween, the casing containing at least one fluid permeable insoluble adsorbent matrix (7) and at least one tracer material (5, 5') located in the fluid passageway. The tracer material (5,5') is a fluid permeable partially soluble material which at least prior to installation is not physically or chemically bonded to the adsorbent matrix (7) and is either mixed with the adsorbent matrix or is located in at least one section (4,4') of the casing (1) separate from but in contact with at least one section (6,6') of the casing holding the insoluble adsorbent matrix (7,7'). The device is intended to be installed in a medium having a fluid path therein.

31 Claims, 7 Drawing Sheets

$A1 = \sin\alpha 1 * A$
$A2 = \sin\alpha 2 * A$
$A3 = \sin\alpha 3 * A$

SAMPLING DEVICE AND METHOD FOR MEASURING FLUID FLOW AND SOLUTE MASS TRANSPORT

TECHNICAL FIELD OF THE INVENTION

The present invention relates to a device and a method for measuring fluid flow and solute mass transport in flow systems.

BACKGROUND OF THE INVENTION

The invention provides for the measurement of solute fluxes and viscous flow in liquid and partially saturated porous media. The solutes may be organic or inorganic molecules that are dissolved and/or attached to dispersed colloids in the liquid. More specifically, the invention relates to the monitoring of solute fluxes in water resources, including, but not limited to, variably saturated soils, sediments and groundwater aquifers, surface water, water for industrial purposes, tap water, drinking water and aqueous waste streams.

Monitoring for solutes in such water resources is often needed to verify concentrations of harmful substances in relation to specific environmental standards or reference levels as proclaimed by the regulating authorities. So, the solutes that are of interest for the present invention represents a very diverse group of organic and inorganic compounds. Depending on the specific environment, they may include for example petroleum or tar-based compounds, halogenated solvents, heavy metals, macronutrients, radionuclides, biocides and their metabolites, surfactants, hormones, pharmaceutical products and their metabolites etc.

The displacement of solute mass in variously saturated porous media occurs by the combination of convection, $J_m$, diffusion, $J_D$, and hydrodynamic dispersion, $J_h$ (Van Genuchten en Wierenga, 1986). The convective transport is the displacement of the solute along with the viscous flow of the liquid, and is described by the equation:

$$J_m = qC \quad (1)$$

where $J_m$ is the convective transport flux (g cm$^{-2}$ s$^{-1}$), q is the volumetric flux density of a viscous fluid (cm$^3$ cm$^{-2}$ s$^{-1}$) and C is the solute concentration (g cm–3).

Solute diffusion results from random Brownian motion of molecules in solutions and in variously saturated media. When the concentration gradient and the volumetric fluid content, θ, are constant, diffusion of a non-sorbing solute may be described by Fick's first law:

$$J_D = -\theta D_m \frac{\partial C}{\partial x} \quad (2)$$

where $J_D$ is the diffusive transport flux (g cm$^{-2}$ s$^{-1}$), θ is the volumetric liquid content of the porous medium (cm$^3$ cm$^{-3}$), $D_m$ is the diffusion coefficient of the porous medium (cm$^2$ s$^{-1}$), and x is the space coordinate. Diffusion in a semi-infinite solution or porous medium does not move the centre of mass of a solute, as the Brownian forces move the molecules away from the centre of mass in all directions. However, in a finite medium with heterogeneous boundaries, diffusion moves the centre of mass away from a source zone and towards a sink zone along the concentration gradient in the medium.

The diffusion coefficient $D_m$ in porous media is always smaller than the diffusion coefficient of the molecule in a free bulk liquid, $D_o$. This is due to the tortuous pathway of the connecting pores, and, among other things, van der Waals interactions with the solid surface. The two diffusion coefficients $D_m$ and $D_o$ are linearly related:

$$D_m = k\theta(L/L_e)^2 D_o \quad (3)$$

where k is an empirical constant, L and $L_e$ are the straight distance between two points and the pathway laid out by the pore system, respectively. Hence, the quadratic term in equation 3 accounts for the pore tortuosity. The relationship between $D_m$ and θ is highly non-linear, because the tortuosity increases with decreasing water content.

Hydrodynamic dispersion results from pore scale heterogeneity of the pore water velocity magnitude and direction. It has been shown that the dispersion effect may be described mathematically similarly to diffusive transport:

$$J_h = -\theta D_h \frac{\partial C}{\partial x} \quad (4)$$

Where $J_h$ is the dispersive transport flux (g cm$^{-2}$ s$^{-1}$), and $D_h$ is the mechanical dispersion coefficient (cm$^2$ s$^{-1}$). The mechanical dispersion coefficient is increasing with increasing fluid velocity according to the empirical relationship:

$$D_h = \lambda v^n \quad (5)$$

Where λ is the dispersivity (cm), v is the pore water velocity (cm s$^{-1}$), that is approximated as q/θ, and n is an empirical parameter, normally equal to 1 (Van Genuchten en Wierenga, 1986). From this relationship it follows that the dispersive flux, unlike the diffusive flux term, vanishes for v→0.

Combining the three terms contributing to the displacement, an expression for the total solute flux, $J_s$, is obtained:

$$J_s = -\theta(D_h + D_m)\frac{\partial C}{\partial x} + qC \quad (6)$$

Substitution of this equation into the equation of continuity for a solute that does not undergo irreversible reactions:

$$\frac{\partial}{\partial t}(\theta C + \rho S) = -\frac{\partial J_s}{\partial x} \quad (7)$$

Yields the general transport equation:

$$\frac{\partial}{\partial t}(\theta C + \rho S) = -\frac{\partial}{\partial x}\left(\theta(D_m + D_h)\frac{\partial C}{\partial x} - qC\right) \quad (8)$$

Where t is time (s), ρ is the bulk density of the porous medium (g cm$^{-3}$), and S is the amount of solute adsorbed to the solute phase (g g$^{-1}$). The simplest form in which sorption to the solid phase can be represented is by instantaneous linear equilibrium conditions:

$$S = K_d C \quad (9)$$

Where $K_d$ is the slope of the linear isotherm (cm$^3$ g$^{-1}$). When considering steady liquid flow in a homogenous porous medium, implying that θ and q are constant in space and time, the transport equation reduces to:

$$\frac{\partial C}{\partial t} = \frac{(D_h + D_m)}{R} \frac{\partial^2 C}{\partial x^2} - \frac{v}{R} \frac{\partial C}{\partial x} \quad (10)$$

Where R is the retardation factor:

$$R = 1 + \frac{\rho K_d}{\theta} \quad (11)$$

Equation 8 may be solved numerically for transient conditions, that is, θ and q varies both in time and space, and dynamic boundary conditions. Numerical solution codes are available both in one and two dimensions. Equation 10 may be solved analytically for constant boundary conditions (e.g. Wierenga and Van Genuchten, 1986).

Gaseous transport in unsaturated porous media occurs due to diffusion processes only, unless pressure gradients are present. The diffusion process may again be described by Fick's first law:

$$J_D = -\theta D_g \frac{\partial C_g}{\partial x} \quad (12)$$

Where $D_g$ is the gaseous diffusion coefficient and $C_g$ is the partial gas concentration in the gas filled pores. Analogue to solute diffusion, the gas diffusion is highly non-linear with respect to the volume contributing to the displacement, i.e. air-filled porosity. Hence, it follows that at a high liquid filled porosity, liquid displacement and solute diffusion dominate the transport process, while at high air-filled porosity, gas-diffusion will dominate the displacement of a volatile compound in the porous medium.

DESCRIPTION OF THE RELATED ART

The most used existing methods for sampling of organic and inorganic substances and/or solutes in soils are soil coring and suction lysimeters. Soil coring simply means that a soil sample is dug out from the ground and analysed. An example of a suction lysimeter is disclosed in U.S. Pat. No. 5,035,149, wherein a porous receptacle is buried in the earth, and an air conduit extends from the earth surface into the receptacle. By drawing a vacuum on the air conduit, soil solution is drawn in from the surrounding soil through the porous walls and is collected in the receptacle. A separate conduit for transferring the soil solution sample brings the sample to the surface when positive air pressure is applied to the receptacle through the air conduit.

Groundwater sampling systems are enclosed in, for example, U.S. Pat. No. 4,745,801 and U.S. Pat. No. 4,759,227 wherein the sampling apparatus is connected to a remote data collection device located above the ground. They do not have an adsorbing material in the sampling device to gather data on the adsorption rates or chemical make-up of the surrounding media.

EP-A-1 094.311 discloses a fluid sampling device especially for sampling water in order to detect parasites therein. The device comprises a cartridge containing a granular filter media, which can be compacted and through which the fluid to be sampled flows. The granular filter media has in a compacted state a pore size less than that of the parasites. The parasites captured can be removed upon expanding and backwashing the granular filter media. This method is clearly not suitable for sampling of organic and/or inorganic solutes, as the method relies on a mechanical filtering process.

The methods described above have in common that the momentaneous solute concentration is measured. Also, these measurements do provide a solute concentration only, and the flux of the compound has to be estimated separately by estimating or calculating the fluid flux.

WO 00/70339 discloses a water sampling method and apparatus for extracting biological and chemical analytes from water. Discrete samples are successively withdrawn with a pumping system from a body of water and an extraction device extracts analyte from the discrete samples and integrates the extracted samples.

For regulatory purposes, there is often interest to measure the solute and/or liquid flux over a longer time period. With momentaneous techniques, a time series of repetitive measurements must be taken to accomplish this, because in most natural flowing media solute concentrations vary strongly with time. Repetitive sampling is a costly operation, hence in practice, monitoring programs, for example in groundwater systems, have to compromise on the number of samples that are taken over a given period.

It would therefore be advantageous to measure integrated solute fluxes over longer time periods. In addition, it would also be advantageous if the measuring device does not require power- and time consuming operations, such as vacuum systems, pumping operations or other power consuming functions.

More recently, passive sampling devices have been introduced. Passive sampling devices make use of mass transfer from the sampled media into the sampling device, by the passive utilisation of solute concentration and/or hydraulic gradients.

There may be distinguished between passive samplers where the mass transfer occurs through a semi-permeable membrane (SPM), impermeable to the sampled liquid but permeable to the investigated solutes (U.S. Pat. No. 5,996,423, WO 92/04646, U.S. Pat. No. 5,904,743). Mass transfer through the semi-permeable membrane is governed by diffusion:

$$J_D = -D_{SPM} \frac{\partial C}{\partial x} \quad (13)$$

where $J_D$ is the flux of the diffusing solute through the SPM (g/cm$^{-2}$ s$^{-1}$), $D_{SPM}$ is the diffusion coefficient of the solute in the membrane (cm$^2$ s$^{-1}$), C is the concentration of the solute in the fluid (g/cm$^{-3}$), and x is the distance parallel to the direction of diffusion. The interior of the sampling device usually consists of a non-polar liquid with high solubility for the solutes that are monitored, thus creating a thermodynamic gradient that controls the diffusion of non-polar compounds in the sampled medium towards the liquid in the SPM device.

Generally, the technical procedure of a SPM device involves installation of the device in the medium of interest, allowing uptake of the solutes of interest over a certain time period, removing the SPM device, and retrieving the accumulated amount of the solute. Thereafter, the concentration of the solute in the surrounding medium is calculated using either equilibrium values or diffusion parameters from equation 13.

Several issues limit the validation and practical applicability of semi-permeable membrane devices. First, the diffusion coefficient in the semi-permeable membranes is dependent on the molecular properties of the solute. This implies that the diffusion coefficient for each single monitored compound should be calibrated individually (Huckins, 1999), which complicates the quantification of the solute concentration. Further, actual diffusion rates may be affected by bio-fouling of the membrane and/or non-ideal diffusion at higher concentrations.

Second, the cumulative diffusion through the SPM is linear over a limited time period only, and this linear period varies individually for different solute molecules (Huckins, 1999). After equilibrating the SPM for a certain period, the uptake of some compounds may still follow the initial linear kinetics, but other compounds will have past the linear stage, hence, quantification of the solute concentration in the fluid medium becomes less accurate, due to the non-linear response.

Third, the concentration of the solute in the fluid medium directly adjacent to the SPM interface, is dependent on the flow rate (Gustavson, 2000) when the flow rate is high enough to compensate for the mass transfer through the SPM, the mass transfer is diffusion-controlled. But, if the flow rate outside the SPM is lower than the mass diffusive transport through the SPM, the solute concentration in the surrounding fluid medium will decrease and the mass transfer through the membrane will be controlled by the liquid flux in the surrounding fluid medium. In this case equation 13 is no longer valid, and the liquid flow rate needs to be known to derive the solute concentration in the fluid medium from the accumulated mass in the SPM device (Gustavson, 2000).

Fourth, SPM devices are not permeable to mobile colloids, as they are only permeable to solutes that are in the free dissolved phase. Organic and/or inorganic colloids can be the primary hosts for transport of strongly sorbing compounds in variously or permanently saturated media and surface water. The sorbing compounds being for example radioactive isotopes, heavy metals and a polar contaminants. For risk assessment purposes, it is important to quantify the entire displaced compound, whether it is in the free dissolved phase or not.

In the second type of passive sampling devices used in liquid systems, the flowing liquid can freely pass the interface between the sampled medium and the sampling device. Examples of such passive sampling devices are disclosed in U.S. Pat. No. 5,355,736 and in WO 01/33173). The sampling device is filled with an insoluble matrix to which the solutes of interest are adsorbed. The accumulated amount of the solute in the sorbing device is, according to WO 01/33173, proposed to be related to the total mass flux into the sampler $$J_s = \frac{M_s}{t_d A_u} \quad (14)$$

in which $J_s$ is the mass flux, $M_s$ is the accumulated amount of the solute adsorbed by the permeable sorbing device, $t_d$ is the time period during which the sorbing device is exposed to the flowing medium, and $A_u$ is an area normal to the direction of the fluid flow that is used to define the fluid flux into the unit.

In WO 01/33173, at least one fluid-soluble resident tracer is introduced in known amounts in the sorbing unit and sorbed on the sorbent before installation of the device in the fluid system. The document describes the case of the sorbing device being a circular column. As fluid passes the permeable device, part of the tracer is transported along with the passing fluid. The method comprises the following set of equations that relates the amount of tracer that is left on the sorbent after a certain period of time, to the amount of fluid that has passed the device:

$$M_r = \frac{2}{\pi}\left[\arcsin\left(\sqrt{1-\xi^2}\right) - \xi\sqrt{1-\xi^2}\right] \quad (15)$$

With $$\xi = \frac{t_d q}{2 r \theta R_d} \quad (16)$$

where $M_r$ is the fraction of the initial mass of tracer remaining, and r is the radius of the sorbing matrix. Three important shortcomings limit the set of conditions for which equation 15 is valid. First, tracer displacement does not only occur due to convective transport, but also due to diffusive transport out of the sampling unit. Second, equation 15 and 16 are based on local equilibrium assumptions (LEA). And, third, transverse diffusion into the sampling unit effects the amount of solute sorbed, $M_s$ (equation 14). Concerning the first issue, it is easy to see that for q→0, $M_r$ in equation 15 remains constant, implying no mass loss of the tracer for zero flow conditions. Hence, equation 15 ignores the effect of the loss of tracer mass from the device due to diffusion. From equation 10 it follows that the relative role of diffusion increases with decreasing liquid velocity, v. Thus, at low liquid velocities, the measurement of tracer loss from the device will be biased with respect to the amount of water that passed the device.

The absolute value of the diffusive flux is proportional to 1/R, but this relation cannot be used to reduce the above-described bias, because the convective flux is also proportional to 1/R (equation 10). Hence, the relative error is the same regardless of the specific R-value of the tracer. Besides, tracers with very high R-values are not very useful for the device described in WO 01/33173, because the relative mass loss occurs very slowly, so that the difference of the initial and final amount $M_r$ cannot be measured accurately.

Second, calculation of the fluid flux (eq. 15-16) relies on the LEA assumption, meaning that instantaneous, linear sorption equilibrium of the tracer is reached at all times (see equation 9). However, LEA is often not valid due to either i) nonlinearity of the sorption isotherm; ii) rate limitations due to surface reactions and/or diffusion in dead-end pores; iii) competition effects, which is important for example for ion-exchange processes; and iv) adsorbent heterogeneity. With q increasing, there comes inevitably a point where the LEA no longer holds, this point representing the higher limit for the application of equation 15, 16. Under normal flow rates, due to the considerations above, the LEA is valid only in macroporous adsorbents. Small, dead-end meso-pores (<50 nm) or micropores (<2 nm) give rise to rate-limited diffusion and high-energy adsorption interactions. These processes invalidate the LEA. But, on the other hand these pores are of high importance because they give rise to high surface areas that strongly increase sorption affinity for solutes of interest, and protect sorbed organic compounds from being biodegraded by micro-organisms migrating along with the fluid. Adsorbent heterogeneity arises when several adsorbents are mixed in the sampling device. In this case, not one single $K_d$ value may be used and the LEA is no longer valid.

A third problem, is that also the transport of solutes in the pore-water into the sorbing device will be biased by transverse diffusion at lower pore water velocities. In fact, some devices make use of this transverse diffusion to derive approximations for the solute concentration in the pore water (e.g. Harper et al. 1997). Diffusion and hydrodynamic dispersion occur transverse to the flow direction through the interface of the sorbing device that is parallel with the flow direction, because there is a constant concentration gradient into the sampling device. While the concentration in the surrounding fluid is C, the solute concentration in the fluid inside the sorbing device will be close to zero, due to the strong sorption properties for the solute of interest.

This transverse mass transfer into the sorbing device is a source of error that invalidates equation 14 in the case that the contribution is significant in comparison to the convective transport of the solute into the sorbing device. The diffusive/dispersive contribution to solute displacement is affected by the diffusion coefficient and concentration gradient in the surrounding medium, while the convective part is controlled by v (equations 6, 8, 10). When taking the discretized form of equation 6, and assuming that the liquid concentration of the pore solute concentration inside the sorbing device is close to zero due to strong sorptive interactions ($\Delta C \approx C$), and conservatively assuming that hydrodynamical dispersion is negligible, it follows that the diffusive flux across the interface of the surrounding medium and the sorbing device, and the convective flux are of equal magnitude if the following equation applies:

$$\frac{(D_m)}{\Delta x} = v \quad (17)$$

Here, $\Delta x$ is the finite diffusion distance over the interface between the surrounding medium and the adsorbent in the sampler The $\Delta x$ is equal to the thickness of the permeable screen surrounding the sorbing device. As an example, molecular diffusion coefficients of charged ions in aqueous solutions are typically around 1e-5 $cm^2s^{-1}$ (Kemper, 1986). Assuming that $\Delta x=0.2$ cm, this would mean that equation 17 applies if the linear fluid velocity is 5e-5 cm $s^{-1}$, equal to 43 mm $day^{-1}$.

In a porous medium, the transverse diffusion from the fluid towards the sorbing devices will then be controlled by the effective bulk diffusion and the second derivative of the concentration with respect to space (equation 10). So, it follows that the error will be largest for solutes with low sorption affinity with the surrounding porous medium. In a liquid, the diffusion towards the sampler will be governed by $D_o$ only.

An example of a porous medium where adverse diffusion mayinvalidate equations 14 and 15 may be taken in the recharge of precipitation to the.groundwater in variably saturated soils. Annual groundwater recharge will typically be below 600 mm $year^{-1}$. So, the average flux below the root zone towards the groundwater will be less than 1.6 mm $day^{-1}$. With the volumetric water content, $\theta$, usually in the range of 0.1-0.3, it follows that average pore water velocities in variably saturated soils typically are below 16 mm $day^{-1}$, which is below the critical value derived above. Hence, in the case of groundwater recharge the results may be strongly influenced by diffusion processes.

SUMMARY OF THE INVENTION

One object of the present invention is to provide a device allowing accurate measurements of fluid flow and solute mass transport in flow systems. The device according to the invention comprises a casing having inlet and outlet openings and a fluid passageway therebetween, said casing containing at least one fluid permeable insoluble adsorbent matrix and at least one tracer material, said tracer material is a fluid permeable partially soluble material which at least prior to installation is not physically or chemically bonded to the adsorbent matrix.

According to one embodiment of the invention, the tracer material is located in at least one section of the casing separate from, but in contact with at least one section of the casing holding said insoluble adsorbent matrix and that the at least one tracer material section and the at least one adsorbent matrix section are located in the fluid passageway between said inlet and outlet openings. In such an embodiment, the tracer material may or may not be physically or chemically bonded to the adsorbent matrix after fluid contact when it starts to dissolve in the fluid and move into the adsorbent matrix section.

In one embodiment of the invention, the device comprises at least two tracer material sections spaced apart and an adsorbent matrix section therebetween, which is in capillary contact with said at least two tracer material sections. With such a device, the diffusion contribution to the tracer mass displacement can be compensated for.

This may also be done with an alternative embodiment of the invention, in which the device comprises at least two adsorbent matrix sections spaced apart and with a tracer material section therebetween, which is in capillary contact with said at least two adsorbent matrix sections.

According to an alternative embodiment, the tracer material and the adsorbent matrix are located in the same section in the casing, wherein the tracer material and the adsorbent matrix are macroscopically mixed with each other. In such an embodiment, the tracer material should not be physically or chemically bonded to the adsorbent matrix, neither before nor after fluid contact, when it starts to dissolve in the fluid.

The tracer material may be chosen from the following groups of materials: inorganic, organic and hybrid organic/inorganic salts; organic, inorganic or hybrid organic/inorganic solids, including polymers, copolymers, block copolymers and oligomers in which hydrolysis of certain bonds can lead to the loss of part of the material; microencapsulated materials in which the tracer with controlled rate is released from the encapsulation in fluids to be measured. According to one aspect of the invention the tracer material is a salt having a solubility product ($K_{sp}$) in the fluid in question of between $10^{-2}$ and $10^{-60}$, preferably between $10^{-2}$ and $10^{-40}$ and more preferably between $10^{-5}$ and $10^{-12}$.

The adsorbent matrix material is an organic, inorganic or hybrid organic/inorganic material having adsorbent properties. According to one aspect of the invention, the adsorbent matrix material is chosen from the following groups of materials: silica, aluminium silicate, aluminium zirconium, metal oxides, synthetic ion exchange resins, carbonaceous materials, zeolites, cellulose, synthetic polymeric materials.

In one embodiment of the invention, the adsorbent matrix material is a hexagonal mesoporous silica.

According to one embodiment, the casing comprises an inlet section and an outlet section adjacent said inlet and outlet openings and respectively, said inlet and outlet sections being located outside and presenting an interfacial area to said adsorbent matrix or tracer material sections, and wherein the projected area normal to the flow direction that contributes to momentum flow into the permeable unit through said inlet opening differs in size from said interfacial area between the inlet section and the adsorbent section or the tracer section.

The device is preferably arranged in a housing, which is impermeable or permeable to fluid. The casing may be removed from the housing for further analysis in the laboratory.

According to one embodiment, two or more devices each comprising a casing with at least one adsorbent matrix section and at least one tracer material sections and inlet and outlet openings are arranged in the same housing. The casings may or may not be angularly displaced with respect to each other. In the latter case, they may contain different tracer materials and/or adsorbent matrix materials.

According to another embodiment, the housing is rotatably connected to a core portion having magnetic properties, said core portion being rotatably connected to a cable or rod intended for the installationof the device.

According to still another embodiment, the housing is provided with a member having a hydrodynamic shape, said housing being rotatably connected to a cable or rod intended for the installation of the device.

In another aspect of the invention, the housing is part of a high-frequency waveguid.e configuration that connects to a coaxial cable.

The invention also provides a method of measuring fluid flow and solute mass transport in flow systems, comprising:

installing in a medium having a fluid path therein a device comprising a casing having inlet and outlet openings and a fluid passageway therebetween, said casing containing at least one fluid permeable insoluble adsorbent matrix and at least one tracer material, allowing fluid to pass from said inlet opening through the adsorbent matrix and tracer material to said outlet opening, wherein the tracer material is a fluid permeable partially soluble material which initially is not physically or chemically bonded to the adsorbent matrix and that upon fluid contact the tracer material will dissolve in the fluid and that after a sampling period the device is removed from the flow system and the amount of tracer material residing in the adsorbent matrix is quantitatively measured to derive therefrom the fluid flow through the device.

According to one embodiment, the tracer material is located in at least one section of the casing separate from but in contact with at least one section of the casing holding said insoluble adsorbent matrix, so that upon fluid contact the tracer material will dissolve in the fluid and be displaced into the adsorbent matrix section, and that after a sampling period the device is removed from the flow system and the amount of tracer material displaced into the adsorbent matrix is quantitatively measured to derive therefrom the fluid flow through the device.

According to one aspect of the invention, solute adsorbed to the adsorbent matrix is quantitatively measured to derive therefrom the concentration of solutes in the fluid flow.

Acdording to a further aspect of the invention, the amount of tracer material displaced into the adsorbent matrix in a direction opposite to the flow direction is quantitatively measured to compensate for diffusion contribution to the tracer mass displacement.

According to still another aspect, the amount of tracer material remaining in the tracer section is quantitatively measured and compared with the amount of tracer material displaced into the adsorbent matrix to derive therefrom diffusion contribution.

According to an alternative embodiment, the tracer material and the adsorbent matrix are located in the same section in the casing, wherein the tracer material and the adsorbent matrix are mixed with each other, and that upon fluid contact, the tracer material will dissolve in the fluid, and that after a sampling period the device is removed from the flow system and the amount of tracer material left in the casing is quantitatively measured to derive therefrom the fluid flow through the device.

In one aspect of the invention, the tracer materials comprise a dispersed inorganic, organic or hybrid inorganic/organic salt of which the positive cation and negative anion do not have sorption affinity for said at least one insoluble adsorbent matrix, such that upon fluid contact, the tracer salt will dissolve into the fluid according to its solubility product, and that after a sampling period, the device is removed from the flow system and the amount of tracer material left in the casing is quantitatively measured to derive therefrom the fluid flow through the device.

In a further aspect of the invention, the method comprises the further step of quantitatively measuring recovery standard material adsorbed to the adsorbent matrix simultaneously with quantitatively measuring solute adsorbed to the matrix, to derive therefrom a more precise measurement of the amount of solute adsorbed to the adsorbent.

According to one embodiment, the method comprises: installing in said medium at different locations thereof, especially different depths, two or more devices each comprising a casing having inlet and outlet openings and at least one adsorbent matrix and at least one tracer material, and that after a sampling period the devices are removed from the medium and analysed separately. Said different devices installed may contain different tracer materials and/or adsorbent matrix materials, to enable detection of different types of solutes.

BRIEF DESCRIPTION OF THE DRAWINGS

The invention will in the following be further described in non-limiting way under reference to the accompanying drawings in which.

DETAILED DESCRIPTION OF THE EMBODIMENTS

Figure 1:
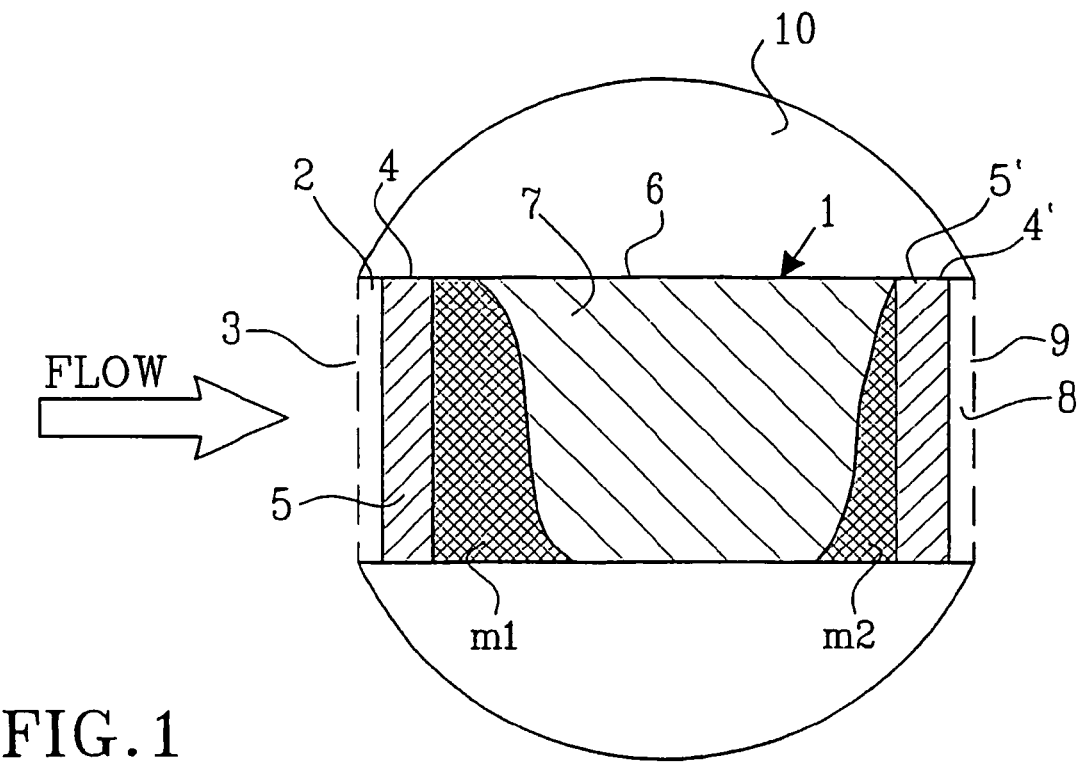
FIG. 1 schematically illustrates one embodiment of a sampling device according to the invention.

The device shown in FIG. 1 represents a simple technical configuration of the sampling device according to the invention. The device contains a casing 1 comprising an inlet section 2 having an inlet opening 3, which preferably is covered with a mesh, a perforated screen or the like, a first permeable tracer section 4 containing at least one partly soluble internal tracer 5 in a known amount and with known diffusion properties, an adsorbent matrix section 6 in the form of a permeable volume filled with an insoluble solid porous matrix 7, comprising of at least one adsorbent material that is particularly suited for the solutes of interest and the used tracers, a second permeable tracer section 4' containing at least one partly soluble internal tracer 5' in a known amount and with known diffusion properties, an outlet section 8 having an outlet opening 9 preferably covered with a mesh, a perforated plate or the like, and a solid housing 10 for the casing 1. The housing 10 may either be made of any appropriate impermeable material, such as stainless steel or a polymer material, such as PTFE or PVC, but the housing 10 may also be made of permeable metallic compounds or organic materials. The latter may be preferred in order to minimize the disturbance of the flow paths of the liquid into the inlet section 2. The casing 1 enclosing the tracer section(s) and adsorbent matrix section(s) is permeable to the liquid only through the inlet and outlet openings 3 and 9. The casing holding the tracer section(s) and adsorbent matrix section(s) is always physically separated from the housing for further analysis in a laboratory.

The areas depicted $m_1$ and $m_2$ schematically illustrate the mass distribution of the tracer displaced into the adsorbent matrix.

The inlet section 2 may contain a non-reactive solid phase matrix, such as, for example, woven mesh material, glass beads, or silica flour of different particle dimensions, which has the function:

in porous media to attain capillary contact of the inlet section with the surrounding porous medium while maintaining sufficiently high fluid conductivity;

in high-flow environments to transform turbulent flow of the entering liquid into laminar flow of the liquid towards the permeable tracer and adsorbent matrix sections 4, 4' and 6.

Capture mobile colloids and avoid clogging of the permeable tracer and adsorbent sections.

As previously mentioned, quantitative monitoring of the cumulative passage of fluid, for example, groundwater, is of prime importance in the device. This quantification can be achieved by using a simple and precise mass balance system based on the dissolution/mobilization of suitable tracers that are initially present in at least one tracer section. The tracer material is preferably, but not limited to, an organic or inorganic or a hybrid organic/inorganic salt that has a solubility product between $10^{-2}$ and $10^{-40}$, with a preferred range between $10^{-5}$ and $10^{-12}$. The solubility product controls the equilibrium of the solid phase with the solution phase, so that always a constant concentration in the solution phase is maintained as long as the solid phase is in contact with solution. Therefore, salts as a tracer source differ fundamentally from adsorbed tracers. From inspection of equation 9, it is clear that for sorption reactions, the solution concentration is dependent on the sorbed concentration and vice versa. Tracer substances should always meet the following criteria:

The tracer is harmless to the fluid environment in which the sampler is installed;

The tracer goes into solution to a constant concentration of the tracer in the passing fluid, regardless of the fluid velocity.

Tracer material is present in negligible amounts in the surrounding fluid environment to which the device is exposed.

The tracer may be effectively retrieved from the adsorbent matrix after the installation and measured with standard analytical techniques.

The following classes of tracers may be distinguished:

A. Tracers based on inorganic salts having a low solubility in water. The advantages of inorganic salts are numerous:

The solubility products ($K_{sp}$) for salt⇋ion equilibria are well known and well defined over a range of temperatures, and change little of the range of temperatures in the environment of the sampler.

There exist many inorganic salts for which $K_{sp}$ values are sufficiently low so that 100% solubilizing of the salt out of the sampler would not occur, but just enough so that the quantity of water passing through the sampler could be measured.

It is easy to employ a combination of inorganic salts so that the error in the quantification of one ion could be compensated by measuring the amount of the other.

Extraction of the remaining ions can be done easily in under laboratory conditions and their concentration can be simply determined by standard analysis methods.

These salts are not affected by microbial degradation.

These salts are very cheap and are produced in high purity in a large scale.

They can be easily incorporated by mutual grinding/mixing into the device.

There are plenty of examples salts that are harmless towards the environment and have low $K_{sp}$ values, for example: $BaF_2$ ($K_{sp}$ $1.84\times10^{-7}$); $BaSO_4$ ($1.08\times10^{-10}$); $BaCO_3$ ($2.58\times10^{-9}$); $CaCO_3$ ($4.96\times10^{-9}$); $CaF_2$ ($1.46\times10^{-10}$); $CaSO_4$ ($7.10\times10^{-5}$); $Ca(OH)_2$ ($4.68\times10^{-6}$); $KClO_4$ ($1.05\times10^{-2}$); $MgCO_3$ ($6.82\times10^{-6}$); $MgF_2$ ($7.42\times10^{-11}$); $MgNH_4PO_4$ ($2.0\times10^{-13}$); $Mg(OH)_2$ ($5.61\times10^{-11}$); $MnS$ ($4.65\times10^{-14}$); $Zn(OH)_2$ ($4.13\times10^{-17}$); $ZnS$($K_{sp}$ $2.93\times10^{-25}$).

B. Tracers based on hybrid organic/inorganic salts. Here, the tracer contains an organic anion and an inorganic cation, or vice versa. The organic ion can, after the dissolution in water, be adsorbed into the adsorbent section of the device and then extracted with the other organic solutes. Likewise, the inorganic ion can be adsorbed, extracted and quantitatively analyzed. Generic structures for hybrid salts could include a suitable cation, for example $Ba^{2+}$, and an organic ion, such as stearate, oleate, or amine. Both the cation and the anion could be monitored in this case. Of course, one could also choose to monitor only the organic or the inorganic tracer. Also, almost any carboxylic acid that it is not too soluble in water can be used. Salts from carboxylic acids are very simple to produce, and there is a large potential of application, since the range of carboxylic acids is huge.

C. Tracers based on organic/organic salts. Here, an organic cation (for example, an ammonium salt such as tetrabutyl ammonium) would be coupled to an organic anion (such as acetate, pivalate, stearate etc). Again, it would be possible to retain either one or both of the ions in the adsorbent section. Also, these types of salts should be selected with respect to favorable dissolution properties, crystal size, sensitivity to pH, and production costs.

D. Tracers based on organic polymers. Here, the tracer displacement is based on the breaking of co-valent bonds by hydrolysis. Possible bonds include, but are not limited to, esters and amides. Polymers can be used that are slightly soluble in water, such as certain (poly)lactic acids or certain (poly)amino acids. Also, block copolymers can be used from a polymer that is soluble in water and one that is not soluble, for example (poly)lactic acid and (poly)ethylene.

E. Microencapsulated materials in which the tracer with a controlled rate is released from the encapsulation in aqueous fluids.

To give some examples, we observed that the dissolution rates of $CaF_2$, Ca-Citrate, $CaHPO_4$, Ca-oleate and Ca-laurate into water were fast enough to reach constant equilibrium values in a variably flow regime in the range from 5 to 128 mm/hr. So, the amount of these salts displaced represented a direct measure for the amount of water passing the sampler, regardless of fluid velocity. This holds as long as diffusion processes may be neglected a device as in FIG. 3 may be used. At lower flow rates, when the role of diffusion becomes more important, a device as in FIG. 1 may be used.

Figure 2:
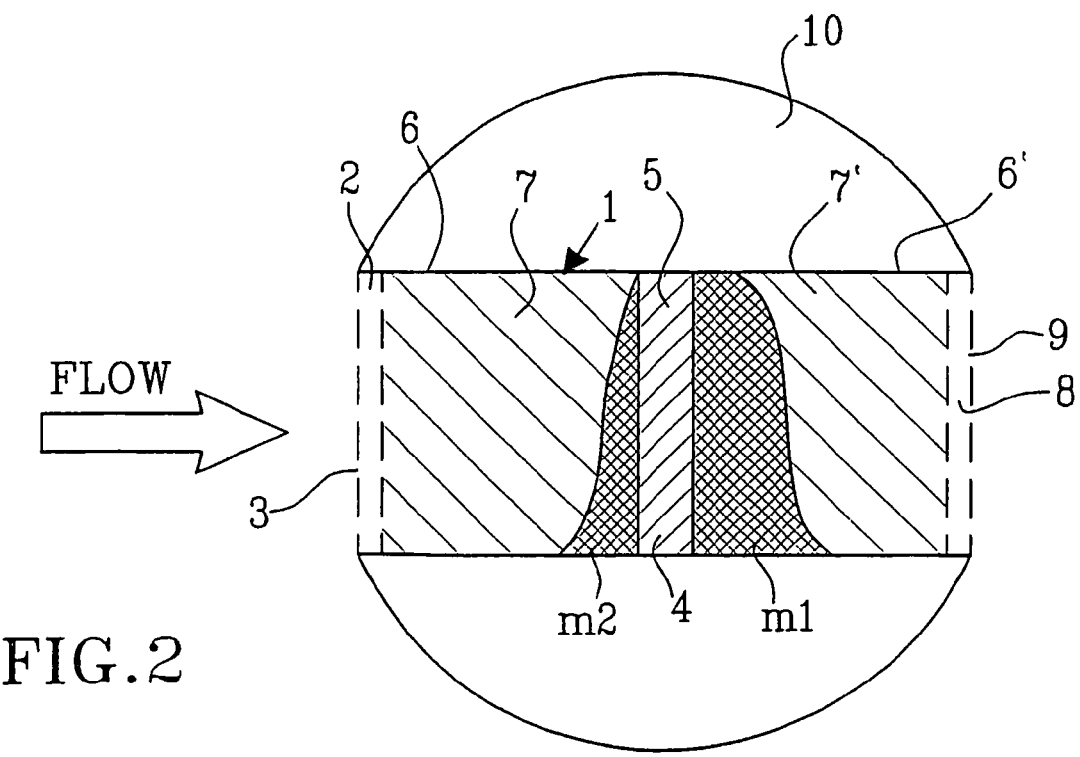
FIG. 2 illustrates another embodiment of a sampling device according to the invention.
Figure 3:
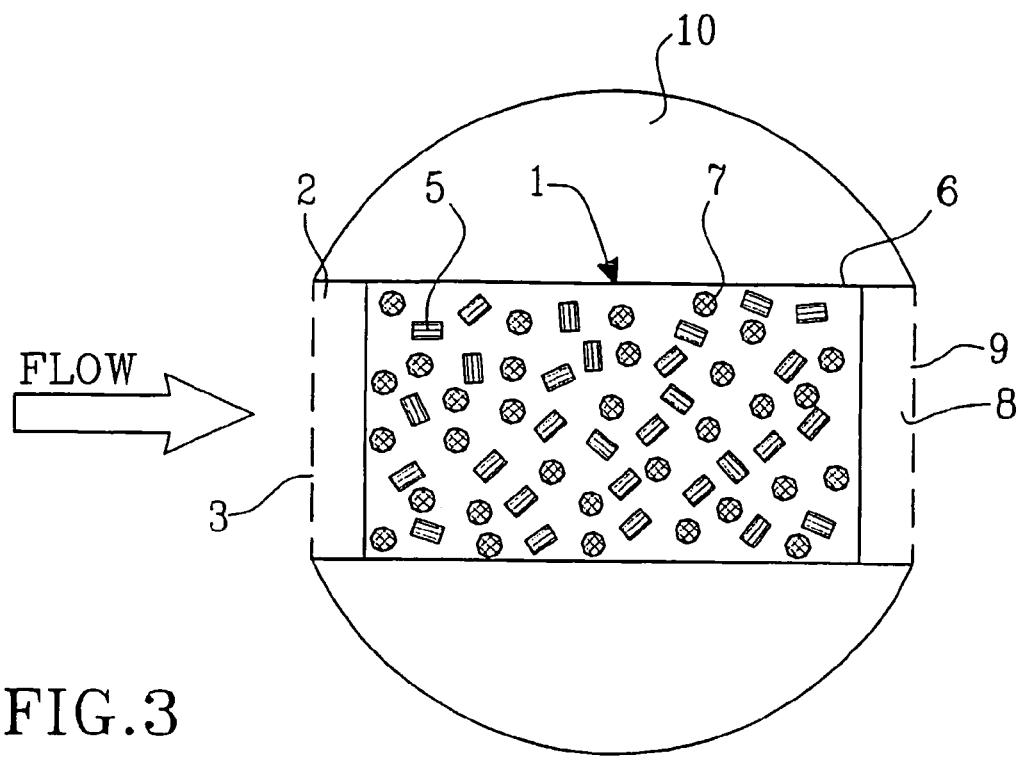
FIG. 3 illustrates a further embodiment of a sampling device according to the invention.

When choosing a salt for the embodiment in FIG. 3, wherein the tracer is mixed with the adsorbent matrix, a salt that does not or that only insignificantly will sorb to the adsorbent matrix before fluid contact as well as after fluid contact, when it has been dissolved by the fluid, should be chosen. One example of a salt from which the ions of the dissolved salt will not sorb or only insignificantly will sorb to commonly used adsorbent matrixes is $CaF_2$. For the embodiment in, for example, FIGS. 1 and 2, wherein the tracer material section(s) is/are separate from the adsorbent matrix section, a salt may be chosen which after fluid contact either will not or will sorb to the adsorbent matrix. For example, sorption interaction include non-specific bonding like Loondon-van der Waals interactions, hydrogen bonding, hydrophobic interaction, but also includes specific bonding, such as ligand exchange, coordinated bonding or ion exchange. Examples of salts that once in solution will adsorb to commonly used adsorbent matrixes are Ca-oleate and Ca-laurate, and also phosphates, like $CaHPO_4$. In these examples it is the anion that will adsorb.

In the device according to FIG. 1, the first tracer 5 moves downstream into the adsorbent matrix section 6 unit as the sum of momentum and diffusion transport, while the second tracer 5' is displaced upstream into the adsorbent matrix section 6 as a result of diffusion counteracting liquid transport. The tracer and adsorbent properties are chosen in such a way, that all the tracer mass flowing into the adsorbent matrix section 6 is retained by the adsorbent matrix 7 within the desirable installation time in the fluid system. The first and second tracers 5 and 5' are preferably chemically different. The use of two different tracers is beneficial for the configuration as in FIG. 1, if one tracer is present in the upstream section of the adsorbent section, and the other in the downstream tracer section.

It is also possible to quantitatively measure the amount of tracer material 5 remaining in the tracer section 4 and compare with the amount of tracer material displaced into the adsorbent matrix 6 to derive therefrom diffusion contribution. In this case, it would be sufficient to use a modified sampling device according to FIG. 1 with only one tracer section 4.

In the device shown in FIG. 2, one permeable tracer section 4 is placed in the middle of the adsorbent matrix section, thus dividing it into first and second adsorbent matrix sections 6 and 6'. This can be beneficial for avoiding release of tracer into the surrounding flow system. Upon fluid contact, tracer 5 is displaced downstream into the second adsorbent matrix section 6' as the sum of momentum diffusion transport and is displaced and upstream into the first absorbent section 6 as a result of diffusion counteracting liquid transport. The tracer displaced into the respective first and second adsorbent matrix sections 6 and 6' is analysed.

The fluid conductivity of the permeable device is controlled, such that the fluid enters the tracer section with a linear velocity v (cm s$^{-1}$). Consider the displacement of a tracer downstream into the adsorbent matrix section 6, with the concentration of the tracer C at the interface between the tracer section and the adsorbent matrix section is constant, $C_o$, and the initial amount of the tracer in the adsorbent matrix section 3 is zero. Then, initial and boundary conditions are:

$$C(x,0)=0 \tag{18}$$

$$C(0,t)=C_oH(t), C(\infty,t)=0$$

where $C_o$ is the concentration of the tracer at the interface of the tracer section and the adsorbent matrix section, and H is the heavyside step function. The adsorbent matrix section is assumed to be of semi-infinite length. The solution is well known:

$$\frac{C(x,t)}{C_o} = \frac{1}{2}erfc\left[\frac{Rx-vt}{2\sqrt{DRt}}\right] + \frac{1}{2}\exp\left[\frac{vx}{D}\right]erfc\left[\frac{Rx-vt}{2\sqrt{DRt}}\right] \tag{19}$$

Where erfc is the complementary error function, and x is the distance increasing in the flow direction. For diffusion of the solute upstream in the adsorbing section, the solution is the same equation 19, except that v is negative:

$$v_{upstream} = -v_{dowstream} \tag{20}$$

If the entire tracer mass that is displaced into the adsorbent section remains, due to sorption, in the adsorbent section during the installation period of the device, the sampler can be regarded as a semi-infinite medium, and the net result of diffusion to the displacement of the centre of mass is zero. Hence, a very useful property may be derived by numerically taking the area under the curves in FIGS. 1 and 2, $m_1$ and $m_2$, representing the mass displaced in the downstream and upstream direction, respectively. The mass $m_1$ and $m_2$ is schematically depicted in FIGS. 1 and 2. It follows that:

$$v = \frac{R}{(C_oT)}\left[\sum_{x=0}^{t} C_x\Delta x - \sum_{x=-1}^{0} C_x\Delta x\right] \equiv \frac{R}{(C_oT)}(m_1-m_2) \tag{21}$$

Where l is the distance from the source of the tracer to the end of the adsorbent section, and $m_1$ and $m_2$ have the unit g cm$^{-2}$. Using the property:

$$v = \frac{V}{AT} \quad (22)$$

It follows that:

$$V = \frac{R}{C_o}(M_1 - M_2) \quad (23)$$

Where $M_1$ and $M_2$ is the mass displaced in the downstream and upstream direction, respectively, now having the unit g. Thus, V may be derived from the mass of a tracer that is displaced upstream and downstream during the installation period, irrespective of the porewater velocity v. It follows from equation 23 that V=0 when $M_1=M_2$ (fully diffusion controlled) and for $M_2 \rightarrow 0$, the solute displacement is fully controlled by convective (momentum) transport.

Likewise, it may be shown that V is a linear function of the mass of tracer a displaced in downstream direction and tracer b in upstream reaction given by:

$$qV + r = \frac{R_a}{C_{o,a}} M_{1,a} - \frac{R_b}{C_{0,b}} M_{2,b} \quad (24)$$

where q and r are calibration parameters. The use of two different tracers is beneficial for the configuration as in FIG. 1, if one tracer is present in the upstream section of the adsorbent section, and the other in the downstream tracer section.

Equations 23 and 24 are used to derive the liquid flow volume in case that diffusive loss from the tracer section cannot be ignored. But in addition, due to the separated tracer source and adsorbent sections, it is possible to obtain another independent mass balance to verify whether counterflow diffusive loss out of the tracer section occurred during the installation period. This is simply done by extracting, after the installation period, both the remaining tracer in the upstream tracer section, and the accumulated tracer amount in the adsorbent section. If the sum of these two equal the initial amount of the tracer before installation, it is obvious that counterflow diffusion may be ignored. In this case, the volume of the liquid may be simply derived from the solubility product of the tracer substance.

FIG. 3 shows an alternative embodiment in which the tracer material 5 and the adsorbent matrix material 7 are located mixed with each other in the same section in the casing 1. The tracer material is not physically or chemically bonded to the adsorbent matrix neither before nor after fluid contact when it starts to dissolve in the fluid. The tracer material should be chosen in accordance herewith.

Preferably the tracer material 5 in this case is a salt. According to one alternative, it is a dispersed inorganic, organic or hybrid inorganic/organic salt of which the positive cation and negative anion do not have sorption affinity for the adsorbent matrix, such that upon fluid contact the tracer salt will dissolve into the fluid according to its solubility product. After a sampling period, the device is removed from the flow system and the amount of tracer material left in the casing is quantitatively measured to derive therefrom the fluid flow through the device.

Quantification of the solute(s) adsorbed by the adsorbent matrix is done in laboratory with routinely available methods, always involving an extraction step and a detection step. The extraction step can be done for example by batch shaking extraction, soxhlet extraction or using vacuum manifold extraction stations. Subsequent detection of the solutes is, for example, done by GC-MS (Gas Chromatography-Mass Spectrometry), HPLC-MS (High Pressure Liquid Chromatography-Mass Spectrometry) or ICP (Inductively Coupled Plasma Emission Spectrometry). An internal recovery standard improves the precision of these procedures, and is required when performing MS quantification. When initially sorbed to the adsorbent matrix, an appropriate internal standard will control for extraction and detection variability. One or more internal standards should be chosen depending on the specific detection method and the range of molecules to be detected. The best internal standard for MS detection is an isotopically labelled version of the solute to be quantified, because it will have a similar extraction recovery, ionisation response, and a similar chromatographic retention time.

The analytical accuracy of the measuring device may be further improved by regulation of the velocity v with which the liquid enters upstream into the tracer section. In low flow systems, it may be desirable to converge the liquid flow paths in the inlet such that the linear flow velocity in the tracer and adsorbent units are increased. This has three major objectives:

To reduce the diffusion contribution to the tracer mass displacement from the tracer source section(s).

To increase effective sampling volume of the surrounding medium contributing to fluid transport into the unit, which is desirable if the fluid flow in the surrounding medium is heterogeneous.

To increase the absolute volume V and mass M that pass the permeable unit within a certain installation period, which is desirable when a low detection limit for the solute under investigation is needed.

Figure 4:
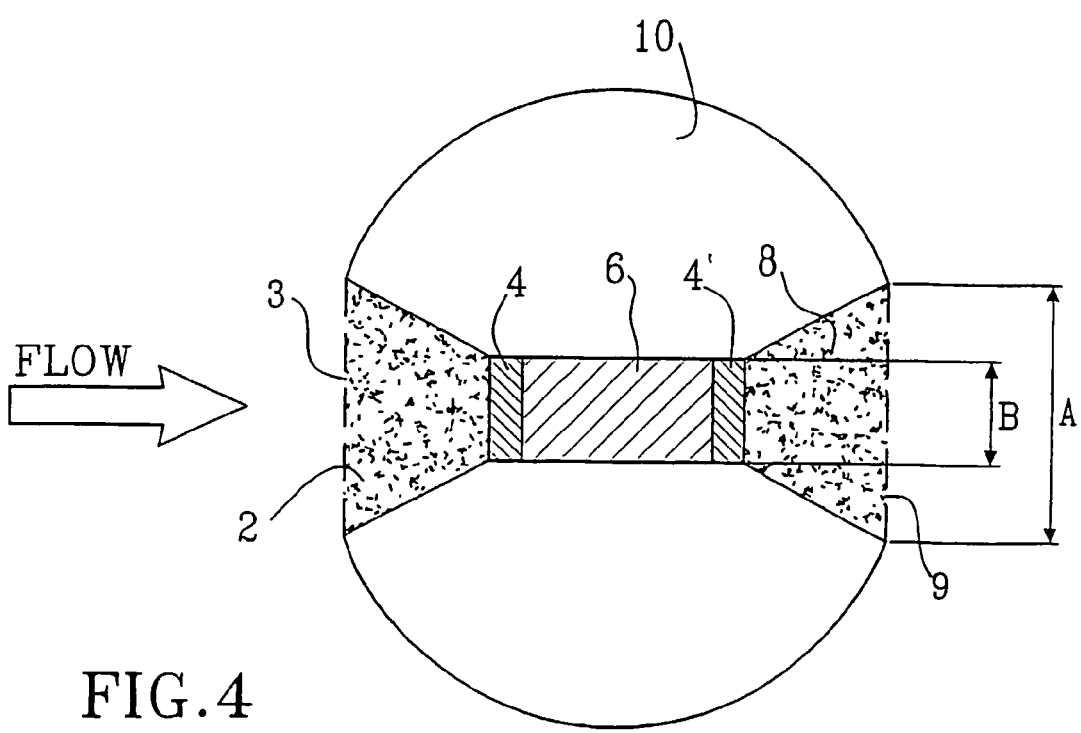
FIG. 4 illustrates an embodiment of a sampling device adapted for low flow systems.
Figure 5:
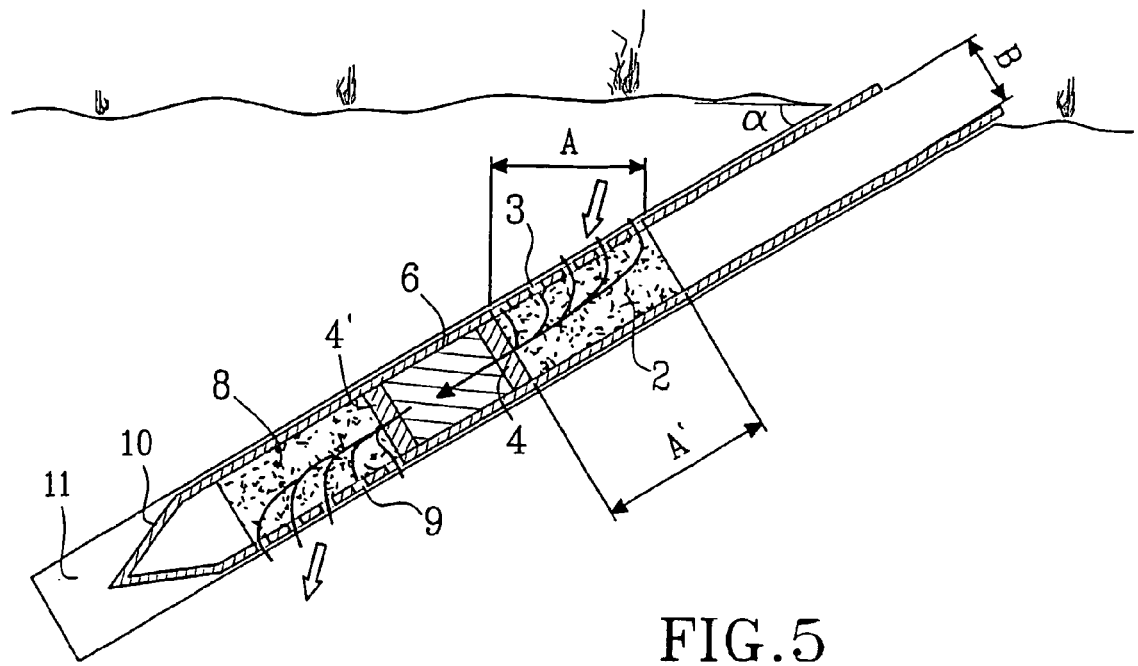
FIG. 5 illustrates an embodiment of a sampling device placed at an angle to the flow direction adapted to low flow systems.

To achieve these objectives, a device, as shown in FIG. 4 or 5, may be used, said device is designed, such that the projected area A>B, where A is the projected area normal to the flow direction that contributes to momentum flow into the inlet section 2, and B is the interfacial area between the inlet section 2 and the tracer section 4. Hence, the flow path of the liquid converge and the linear velocity v at the intersection B is A/B times higher than the velocity v of the liquid at the interface of the surrounding medium and the inlet of the sampling device. This assumes that the hydraulic conductivity of the permeable section does not limit the flow into the permeable unit.

In case the sorbing unit is installed perpendicular to the flow direction A=A', where A' is the area in direct contact with the flowing liquid/porous medium (FIG. 3). Alternatively the sorbing unit may be installed in an angle to the flow direction, such that A=A' cos($\alpha$), where $\alpha$ is the angle of installation, as is shown in FIG. 5.

In high flow systems, it may be desirable to diverge the liquid flow paths in the inlet, such that the linear flow velocity in the tracer and adsorbent units are decreased. This has three major objectives:

To avoid turbulent flow and high hydrodynamic dispersion in the tracer and the adsorbent sections of the device.

To assure that the tracer dissolution may reach equilibrium with the passing fluid.

To increase the residence tinte of the liquid in the adsorbent unit, such that all of the passing solutes can be adsorbed.

To achieve these objections, the unit is designed, such that the projected area A<B, as is shown in FIG. 5, where A is again the projected area normal to the flow direction that contributes to momentum flow into the permeable unit, and B is the interfacial area between the inlet section 2 and the tracer section 4. Hence, the flow path of the liquid diverges and the linear velocity v at the intersection B is A/B times smaller than the velocity of the liquid at the interface of the surrounding medium and the inlet of the sampling device. The sorbing unit may be either installed normal to the flow direction; in this case A=A', where A' is the area in direct contact with the flowing liquid/porous medium. Or, the sorbing unit may be installed in an angle to the flow direction, such that A=A'·cos($\alpha$), where $\alpha$ is the angle of installation.

In flow systems where the liquid flow direction is known a priori, the permeable unit is oriented parallel or in an angle to the flow direction, however, always such that an inlet and an outlet are exposed to the surrounding fluid or porous medium in the upstream and downstream direction, respectively. It is in most cases important that the position of the permeable unit is fixed during the installation. This orientation and fixation maybe attained by different ways, depending on the flow environment.

Typical low flow environments include variously saturated soils and packed bed reactors, for which the flow direction is usually known. A device, such as in FIG. 5, may then be installed by making a bore hole 11 with standard auger equipment, and inserting the device into the bore hole 11. The inlet and outlet sections 2 and 8 should obviously be in capillary contact with the surrounding soil, and positioned in the upstream and downstream direction of the fluid flow, respectively. The angle of installation to the main flow direction is then recorded.

Figure 10:
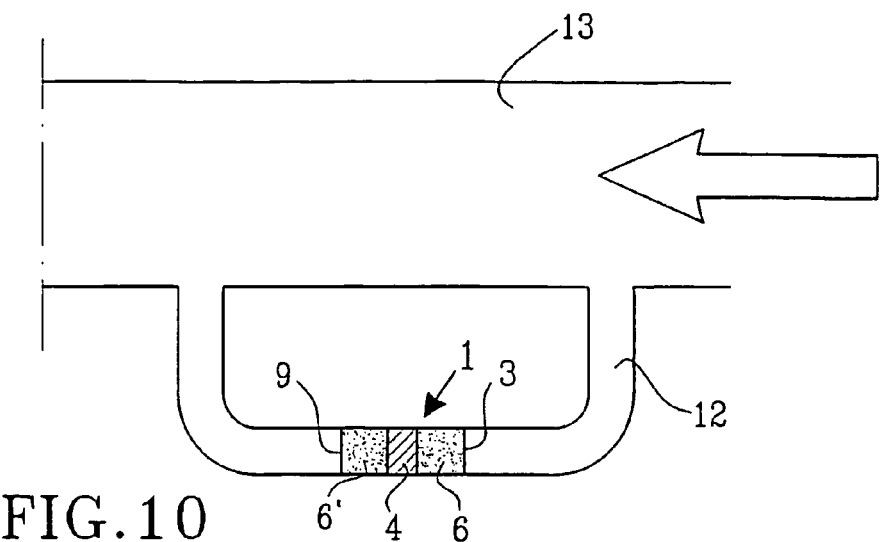
FIG. 10 illustrates an embodiment wherein a sampling device is installed in a bypass conduit.

In high flow pipelines or tubings, the fluid flow direction is also known in advance, and the device may be attached to the interior of the pipeline or be installed as an inline configuration. Alternatively, the installation may be done by constructing a bypass pipeline or tubing 12, which contains a smaller part of the total liquid flow through a pipeline 13, for example a drinking water pipeline, as shown in FIG. 10, or in a large container, for example a freshwater container.

Figure 7:
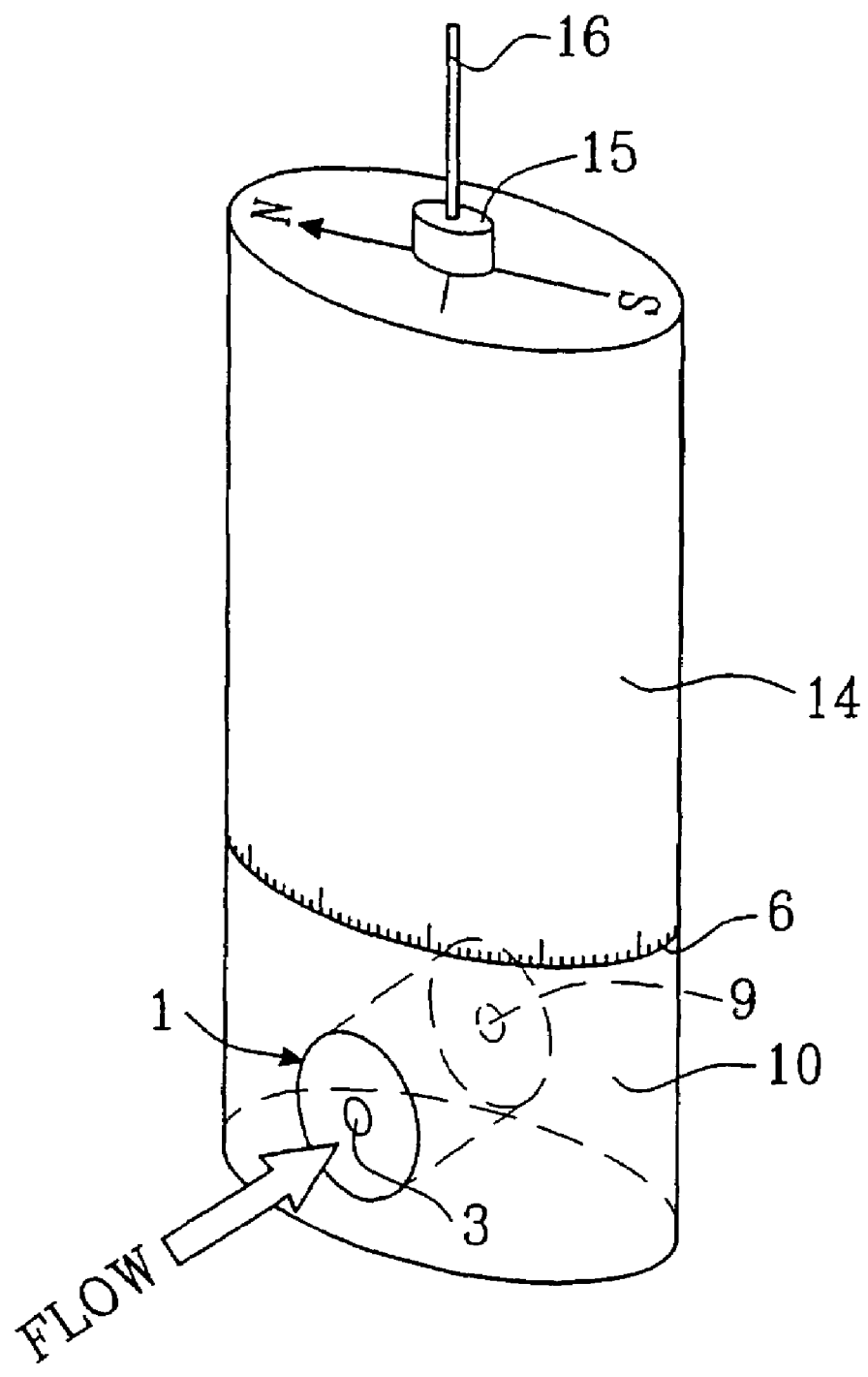
FIG. 7 illustrates an embodiment of a sampling device according to the invention adapted for flow systems in which the flow direction is constant in time.

In other systems, like groundwater aquifers, medium-velocity horizontal transport ($\approx$10-200 m year) typically occurs, and the flow direction is normally constant in time, and may be measured using other devices before installing the device. An example of a suitable device is shown in FIG. 7 and comprises a core portion 14 having magnetic properties, said core portion 14 is rotatably connected to a housing 10 holding at least one sampling device 1 with inlet and outlet openings 3 and 9. In this case, the device may be installed in a vertical borehole casing, and may be fixated by giving the core portion 14 magnetic properties. The inlet and the outlet openings 3 and 9 are in a desired fixed position with respect to spatial coordinates during the installation, as the housing 10 holding the sampling device 1 can be rotated with respect to the core portion 14. The core portion 14 can rotate freely into the fixed coordinate position due to a rotation joint 15 connected to a cable or rod 16 that is used to place the device at a certain depth in the liquid system.

Figure 8:
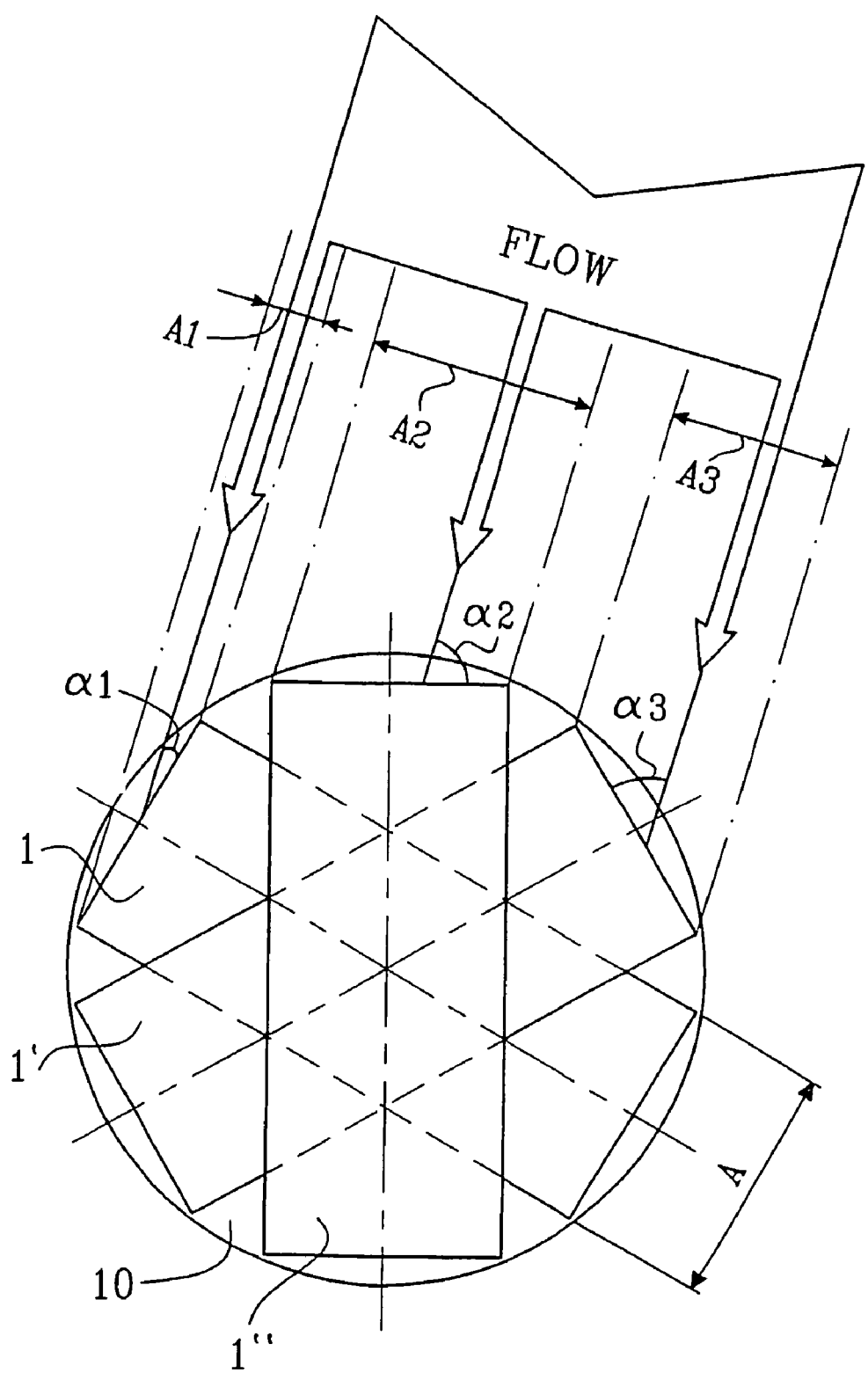
FIG. 8 illustrates an embodiment of a sampling device according to the invention adapted for flow systems in which the flow direction is not known.

If the fluid flow direction in medium or low-flow environments is not known a priori, the device may consist of two or more, for example three, identical sampling devices 1, 1' and 1" all containing previously described tracer sections and adsorbent sections, as is shown in FIG. 8. The sampling devices 1, 1' and 1" are arranged in the same housing 10 and are oriented in a 60° angle with respect to each other. Hence, the areas contributing to the inflow into the permeable units is proportional to sin($\alpha$), where $\alpha$ is the angle of the inlet with the flow direction. If only the concentration of the solute in the surrounding medium is of concern, only the one sampling device through which most water has passed during installation, has to be analysed for solute and tracer mass displaced into this unit. The tracer sections may contain colour or fluorescent dye so that easily can be distinguished for which of the sampling devices $\alpha$ is most close to 90°. If both the solute concentration and the flow direction of the fluid are of concern, all three permeable units should be analysed for the tracer amounts, and the flow angle may be derived from the relative amounts of tracer displaced.

It would also be possible to arrange two or more sampling devices 1 in the same housing 10, said sampling devices containing different tracers and or adsorbent matrix materials, in order to measure different types of chemicals. In this case, the sampling devices are not angularly displaced in the housing with respect to each other.

Figure 6:
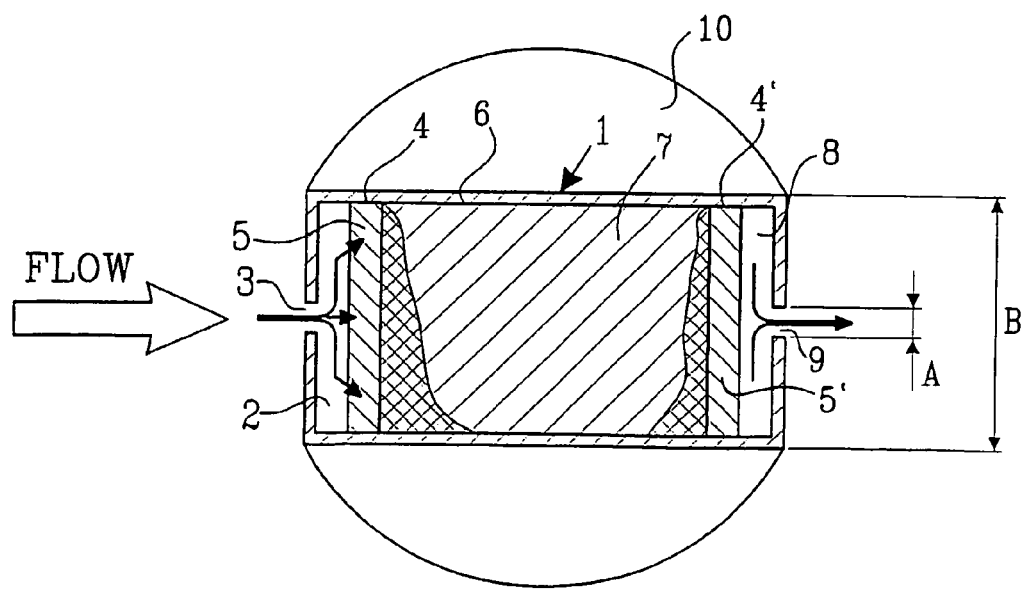
FIG. 6 illustrates another embodiment of the sampling device adapted for high flow systems.
Figure 9:
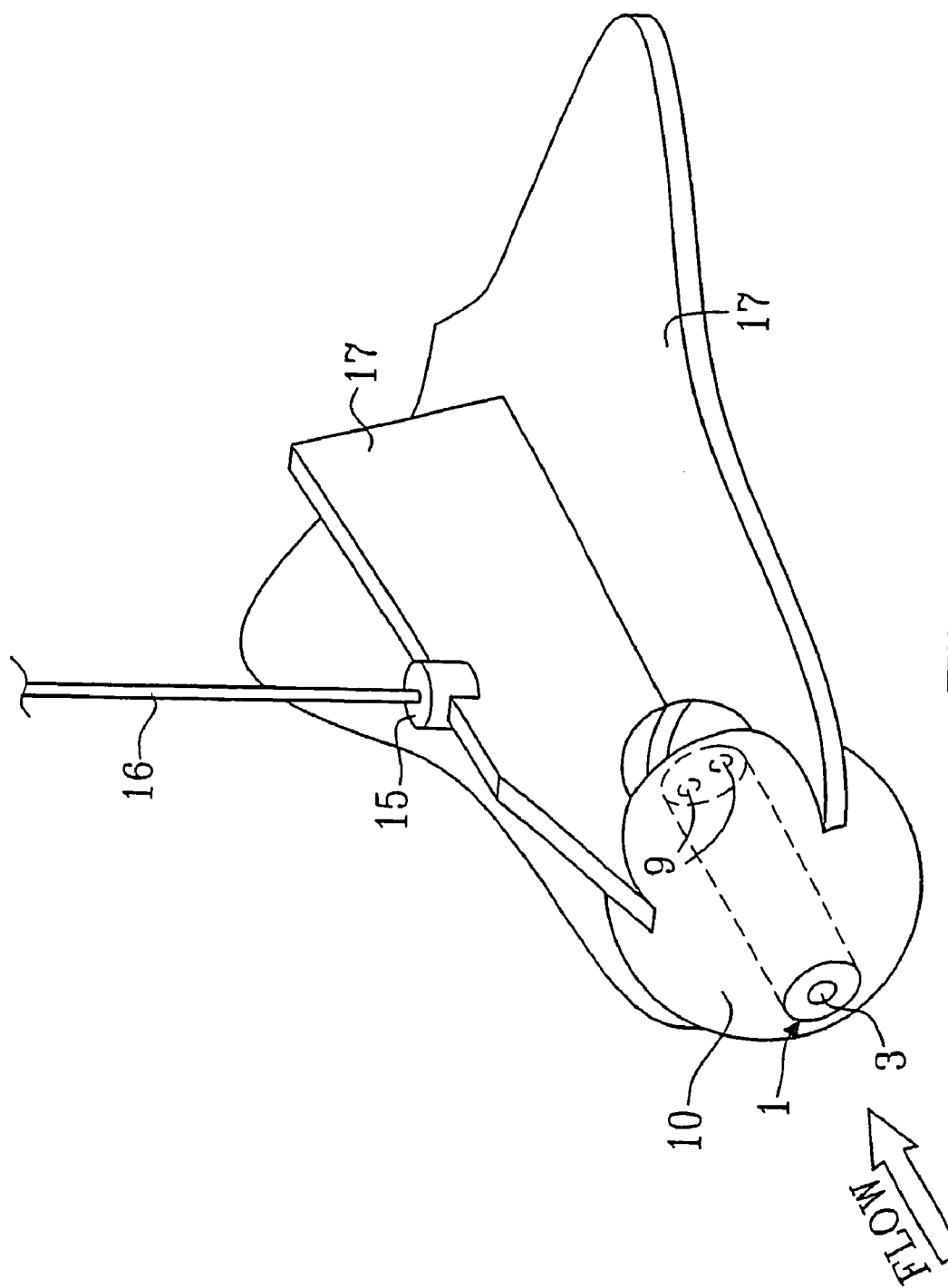
FIG. 9 illustrates an embodiment of a sampling device according to the invention adapted for high flow systems with shifting flow directions.

In high flow liquid environments with shifting flow direction, such as steams, rivers, drinking water storage containers, or tidal areas, the orientation of the inlet and outlet of the device towards the flow direction may be achieved by giving the device a special hydrodynamic shape comprising a rudder member 17 as is illustrated in FIG. 9. The housing itself may also be given a hydrodynamic shape. This shape guarantees that the hydrodynamic resistance of the device is at minimum when the inlet of the device is upstream. Hence, the inlet of the device will always be upstream, even if the flow direction is changing during the installation time. The inlet openings 3 of the sampling devices 1 may be dimensioned such that the liquid velocity of the liquid in the sampler is reduced, similar to FIG. 6.

It is recognised that the hydraulic conductivity of the permeable units also may be used to regulate the flow rate through the permeable unit.

As the volume fraction of the liquid in partially saturated media is of paramount importance for the transport of volatile compounds, a simultaneous measurement of the solute flux, water flux and volumetric fluid content would be of large practical value for the quantification of the gas and solute flux in the porous medium. The measurement of the volume fraction of the liquid in the porous medium can be achieved by assembling the device as a central metal core or tube, with an isolated metal wire wrapped around the central metal core, connecting the central core and the isolated wire to a coaxial cable, and measuring the travel speed of a high frequency electromagnetic block or pulse wave through the quasi-coaxial system that the measuring unit represents. The velocity of the electromagnetic wave is related to the dielectric constant of the surrounding porous medium, that in turn is related to the volume fraction of the liquid in the surrounding medium. This technique, known as TDR (Time Domain Reflectometry) has become a very popular monitoring instrument for measurements of water contents in the variously saturated zone. Different geometrical configurations of TDR probes do exist, all of which in principle may be used in combination with the invention. Such a combined probe would then be used to simultaneously measure the accumulated solute flux and the dynamics of the water content in the soil.

Like mentioned before, the complete adsorption of the solutes of interest in the permeable device is a prerequisite for proper solute flux measurements, however, this is in practice not a trivial task. The requirements for the adsorbent materials are:

very high sorption affinity for the solute of interest.

Rapid sorption kinetics, so that sorption equilibrium is attained during the passage of the fluid through the device.

Excellent extraction efficiency, which means that the solutes of interest can be completely extracted from the adsorbent material in the laboratory with standard laboratory techniques.

Good wetting properties for the liquid passing the permeable device. For example, if the adsorbent would be water-repellent, the hydraulic conductivity of the device would be strongly reduced, rendering these adsorbents not useful for applications in aqueous systems.

Hexagonal Mesoporous Silica (HMS, sometimes called MCM for Mobil Composite Materials) is a uniquely structured silicon-oxygen polymer (that may or may not contain aluminium or other metal atoms) that is synthetisized using the templated sol-gel method (U.S. Pat. No. 5,215,737). Its special structural properties include very high specific surface area (up to 800 $m^2g^{-1}$) and hexagonal arrays of 'wormhole' shaped nanopores. These pores are a direct result of the synthesis method, which is based on the self-assembly of silica monomers around rod-like micelles formed through hydrophobic interactions between the amine (the template) chains. Although the synthesis of HMS materials is simple, the lattice growth depends on many different parameters, such as type of template, solvent composition, temperature, stirring regime, ageing time, and silicon or aluminium precursor(s) employed.

Specifically to the current invention, to give one example, the calcination step was found to have a dramatic effect on the sorption capacity of the material towards phenanthrene. The preparation of HMS materials with specific structural variables lies somewhere between science and art. That being said, once a particular formulation for preparation of an HMS material has been established, reproducing similar batches is not difficult. The high activity of HMS materials materials in the sorption of non-polar compounds, including phenanthrene, N-propyl-N-[2-(2,4,6-trichlorophenoxy)ethyl]imidazole-1-carboxamide (Prochloraz, a fungicide), di(2-ethylhexyl)phthalate (DEHP, plastic softener) and polar compounds, e.g. 4-(2-dodecyl)-benzensulfonic acid, Na salt (LAS, surfactant), makes them ideal candidates for the present invention. What is more, these materials are biologically and environmentally inert, and in fact are composed almost entirely of silicon and oxygen.

Although HMS is an ideal candidate for the use as adsorbent matrix material other adsorbents may be more suited for specific solutes. Further examples of adsorbents that may be used are silica, aluminium silicate, aluminium zirconium, metal oxides, synthetic ion exchange resins, carbonaceous materials, zeolites, carbohydrates and synthetic polymers, for example polystyrene, polyethylene, polytetra fluoro ethylene.

Preferred examples of metal oxides are transition metal oxides, for example, zirconia, titania, and/or lanthanide metal oxides (for example ceria) with the general formula $A_xB_yC_zO_w$, where O is oxygen and A, B and C are transition metals or lanthanides.

Preferred examples of carbohydrates are polysaccharides, for example, cellulose.

Figure 11:
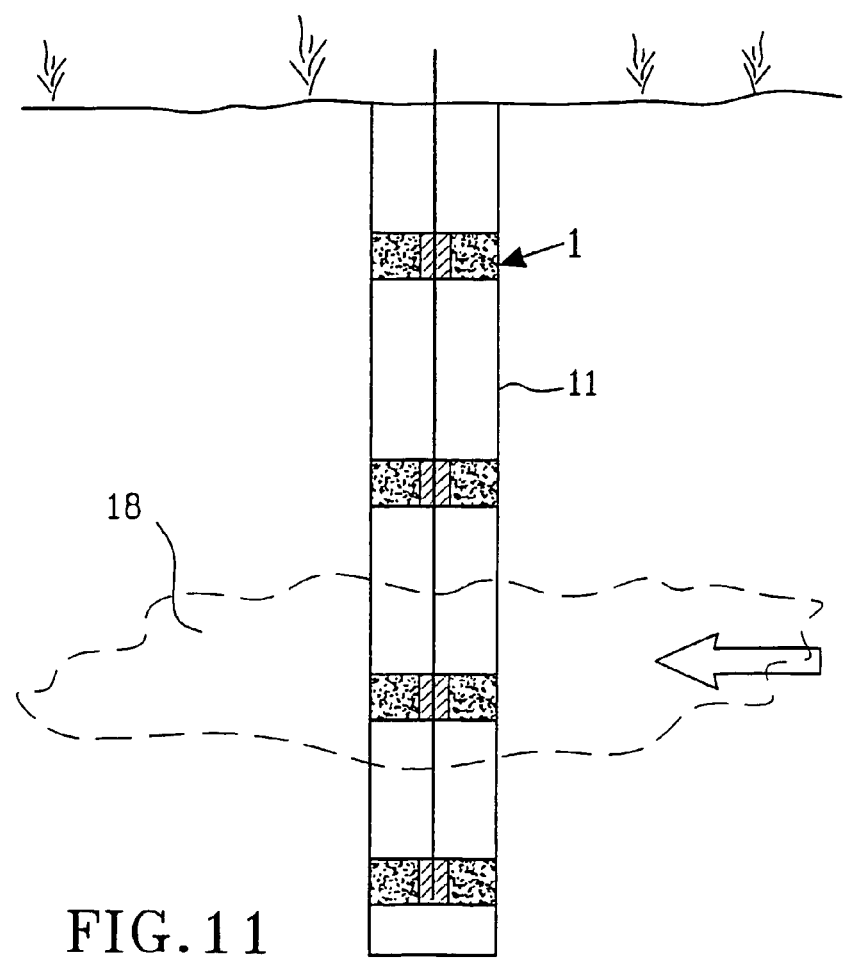
FIG. 11 illustrates an embodiment wherein several sampling devices are installed at different depths.

Two or more sampling devices may be installed at different locations, especially different depths, in the medium to be investigated. This is illustrated in FIG. 11. These sampling devices are, after the sampling period, removed from the fluid medium and analysed separately. It will then be possible to detect in which location(s) of the medium a fluid flow and/or certain solutes 18 are present. Different tracer materials and/or adsorbent matrix material may be used in the different sampling casings to measure different types of solutes.

The invention is not limited the shown embodiments but can be varied in a number of ways without departing from the scope of the appended claims and the arrangement and the method can be implemented in various ways depending on application, functional units, needs and requirements etc.

The invention claimed is:

1. A device for measuring fluid flow and solute mass transport in flow systems, comprising a casing (1) having inlet (3) and outlet (9) openings and a fluid passageway therebetween, said casing containing at least one fluid permeable insoluble adsorbent matrix (7) and at least one tracer material (5, 5'), characterized in that the tracer material (5,5') is a fluid permeable partially soluble material which at least prior to installation is not sorbed to the adsorbent matrix (7).

2. A device as cLaimed in claim 1, characterized in that the tracer material (5,5') is located in at least one section (4,4') of the casing (1) separate from but in contact with at least one section (6,6') of the casing holding said insoluble adsorbent matrix (7,7') and that the at least one tracer material section (4,4') and the at least one adsorbent matrix section (6,6') are located in the fluid passageway between said inlet (3) and outlet openings (9).

3. A device as claimed in claim 2, characterized in that the device comprises at least two tracer material sections (4,4') spaced apart and an adsorbent matrix section (6) therebetween, which is in contact with said at least two tracer material sections (4.4').

4. A device as claimed in claim 3, characterized in that the tracer materials (5,5') in the at least two tracer material sections (4,4') are chemically different.

5. A device as claimed in claim 2, characterized in that the device comprises at least two adsorbent matrix sections (6,6') spaced apart and with a tracer material section (4) therebetween, which is in contact with said at least two adsorbent matrix sections.

6. A device as claimed in claim 1, characterized in that the tracer material (5) and the adsorbent matrix (7) are located in the same section in the casing (1), wherein the tracer material and the adsorbent matrix are mixed with each other.

7. A device as claimed in claim 6, characterized in that at least one recovery standard material is adsorbed to the at least one insoluble adsorbent matrix (7).

8. A device as claimed in claim 1, characterized in that the tracer material (5, 5') is chosen from the following groups of materials: inorganic, organic and hybrid organic/inorganic salts; organic, inorganic or hybrid organic/inorganic solids, including polymers, copolymers, block copolymers and oligomers in which hydrolysis of certain bonds can lead to the loss of part of the material; microencapsulated materials in which the tracer with controlled rate is released from the encapsulation into fluids to be measured.

9. A device as claimed in claim 8, characterized in that the tracer material (5, 5') is a salt having a solubility product ($K_{sp}$) in the fluid in question of between $10^{-2}$ and $10^{-60}$.

10. A device as claimed in claim 9, characterized in that the tracer material (5, 5') is chosen from the following group of salts: $CaF_2$, Ca-Citrate, $CaHPO_4$, Ca-oleate and Ca-laurate.

11. A device as claimed in claim 1, characterized in that the adsorbent matrix material (7,7') is an organic, inorganic or hybrid organic/inorganic material having adsorbent properties.

12. A device as claimed in claim 11, characterized in that the adsorbent matrix material (7,7') is chosen from the following groups of materials: silica, aluminium silicate, aluminium zirconium, metal oxides, synthetic ion exchange resins, carbonaceous materials, zeolites, carbohydrates, synthetic polymeric materials.

13. A device as claimed in claim 12, characterized in that the adsorbent matrix material is a hexagonal mesoporous silica.

14. A device as claimed in claim 1, characterized in that the casing (1) comprises an inlet section (2) and an outlet section (8) adjacent said inlet and outlet openings (3) and (9) respectively, said inlet and outlet sections being located outside and presenting an interfacial area (B) to said adsorbent matrix and/or tracer material sections (6) and (4), and wherein a projected area (A) normal to the flow direction contributes to momentum flow into the permeable unit through said inlet opening (3) differs in size from said interfacial area (B) between the inlet section (2) and the adsorbent section (6) or the tracer section (4).

15. A device as claimed in claim 1, characterized in that the casing (1) is arranged in a housing (10) which is impermeable or permeable to fluid, said casing being removable from the housing.

16. A device as claimed in claim 15, characterized in that two or more devices each comprising a casing (1, 1' and 1") with at least one adsorbent matrix section (6) and at least one tracer material sections (4) or a combined adsorbent matrix and tracer material section respectively, and inlet (3) and outlet (9) openings are arranged in the same housing (10).

17. A device as claimed in claim 16, characterized in that said casings (1, 1' and 1") are oriented angularly displaced with respect to each other.

18. A device as claimed in claim 16, characterized in that said casings (1, 1' and 1") contain different tracer materials (5) and/or adsorbent matrix materials (7).

19. A device as claimed in claim 15, characterized in that the housing (10) is rotatably connected to a core portion (14) having magnetic properties, said core portion (14) being rotatably connected (15) to a cable or rod (16) intended for the installation of the device.

20. A device as claimed in claim 15, characterized in that the housing (10) is provided with at least one member (17) having a hydrodynamic shape and/or the housing itself having a hydrodynamic shape.

21. A device as claimed in claim 15, characterized in that the housing (10) is part of a high-frequency waveguide configuration that connects to a coaxial cable.

22. A method of measuring fluid flow and solute mass transport in flow systems, comprising:
installing in a medium having a fluid path therein a device comprising a casing (1) having inlet (3) and outlet (9) openings and a fluid passageway therebetween, said casing containing at least one fluid permeable insoluble adsorbent matrix (7,7') and at least one tracer material (5, 5'), allowing fluid to pass from said inlet opening through tlie adsorbent matrix and tracer material to said outlet opening, characterized in that the tracer material (5,5') is a fluid permeable partially soluble material which at least prior to installation is not sorbed to the adsorbent matrix (7) and that upon fluid contact the tracer material will dissolve in the fluid and that after a sampling period the device is removed from the flow system and the amount of tracer material residing in the adsorbent matrix is quantitatively measured to derive therefrom the fluid flow through the device.

23. A method as claimed in claim 22, characterized in that the tracer material (5,5') is located in at least one section (4,4') of the casing (1) separate from but in contact with at least one section (6,6') of the casing holding said insoluble adsorbent matrix (7,7'), so that upon fluid contact the tracer material will dissolve in the fluid and be displaced into the adsorbent matrix section, and that after a sampling period the device is removed from the flow system and the amount of tracer material displaced into the adsorbent matrix is quantitatively measured to derive therefrom the fluid flow through the device.

24. A method as claimed in claim 23, characterized in that the amount of tracer material (5, 5') displaced into the adsorbent matrix (7, 7') in a direction opposite to the flow direction is quantitatively measured to compensate for diffusion contribution to the tracer mass displacement.

25. A method as claimed in claim 23, characterized in quantitatively measuring amount of tracer material (5, 5') remaining in the tracer section (4,4') and comparing with the amount of tracer material displaced into the adsorbent matrix (6,6') to derive therefrom diffusion contribution.

26. A method as claimed in claim 22, characterized in that the tracer material (5,5') and the adsorbent matrix (7) are located in the same section in the casing (1), wherein the tracer material and the adsorbent matrix are mixed with each other, and that upon fluid contact the tracer material will dissolve in the fluid and that after a sampling period the device is removed from the flow system and the amount of tracer material left in the casing is quantitatively measured to derive therefrom the fluid flow through the device.

27. A method as claimed in claim 26, characterized in that that the tracer material (5,5') is a dispersed inorganic, organic or hybrid inorganic/organic salt of which the positive cation and negative anion do not have sorption affinity for said at least one insoluble adsorbent matrix (7), such that upon fluid contact the tracer salt will dissolve into the fluid according to its solubility product, and that after a sampling period the device is removed from the flow system and the amount of tracer material left in the casing is quantitatively measured to derive therefrom the fluid flow through the device.

28. A method as claimed in claim 22, characterized in quantitatively measuring solute adsorbed to the adsorbent matrix to derive therefrom the concentration of solutes in the fluid flow.

29. A method as claimed in claim 28, characterized in quantitatively measuring recovery standard material adsorbed to the adsorbent matrix simultaneously with quantitatively measuring solutes adsorbed to the matrix, to derive therefrom a more precise measurement of the amount of solute adsorbed to the adsorbent.

30. A method as claimed in claim 22, characterized in installing in said medium at different locations thereof, especially different depths, two or more devices each comprising a casing (1) having inlet (3) and outlet (9) openings and at least one adsorbent matrix (7,7') and at least one tracer material (5,5'), and that after a sampling period the devices are removed from the medium and analysed separately.

31. A method as claimed in claim 30, characterized in that the different devices installed contain different tracer materials (5,5') and/or adsorbent matrix materials (7,7').

* * * * *